United States Patent [19]

Pipes

[11] Patent Number: 5,021,235

[45] Date of Patent: Jun. 4, 1991

[54] PREPARATION OF RHENIUM PHOSPHONATE THERAPEUTIC AGENTS FOR BONE CANCER WITHOUT PURIFICATION

[75] Inventor: David W. Pipes, St. Louis, Mo.

[73] Assignee: Mallinckrodt, Inc., St. Louis, Mo.

[21] Appl. No.: 346,411

[22] Filed: May 2, 1989

[51] Int. Cl.$^5$ .................. A61K 43/00; C01G 47/00
[52] U.S. Cl. .............................. 424/1.1; 423/249; 534/10
[58] Field of Search ................ 424/1.1; 534/10; 423/249

[56] References Cited

U.S. PATENT DOCUMENTS

| | | | |
|---|---|---|---|
| 3,192,011 | 8/1963 | Cooper | 23/22 |
| 3,983,227 | 9/1976 | Tofe et al. | 424/1.1 |
| 4,652,440 | 3/1987 | Paik et al. | 424/1.1 |
| 4,778,672 | 10/1988 | Deutsch et al. | 424/1.1 |
| 4,925,925 | 5/1990 | Deutsch | 424/1.1 X |

FOREIGN PATENT DOCUMENTS 250966  1/1988  European Pat. Off. .

OTHER PUBLICATIONS

Mathieu et al., *Int. J. Appl. Radiat. Isot.* 30: 25–27 (1979).
Eisenhut, *Int. J. Appl. Radiat. Isot.* 33: 99–103 (1982).
Weininger et al., *Nucl. Med.* 23: 81–82 (1984).
Ketring, *Nucl. Med. Biol.* 14: 223–232 (1987).
Maxon et al., *Radiology* 166: 501–507 (1988).

*Primary Examiner*—John S. Maples
*Attorney, Agent, or Firm*—Rothwell, Figg, Ernst & Kurz

[57] ABSTRACT

The process of the present invention includes preparing a first aqueous solution of rhenium in the form of radioactive perrhenate, wherein the concentration of rhenium in said solution is within the range of about $5 \times 10^{-6}$M to about $2 \times 10^{-3}$M, and then reducing and complexing the radioactive perrhenate by mixing a second solution or lyophilized solid with the first solution. The second solution or lyophilized solid comprises a ligand which complexes with the radioactive perrhenate and a reductant wherein the reductant is present in the second solution at a concentration in the range of about 0.005M to about 0.020M and the ligand is present in the second solution at a concentration in the range of about 0.01M and about 0.15M. The pH of the resultant solution is within the range of about 1.5 to about 5.5.

9 Claims, No Drawings

PREPARATION OF RHENIUM PHOSPHONATE THERAPEUTIC AGENTS FOR BONE CANCER WITHOUT PURIFICATION

FIELD OF THE INVENTION

The present invention relates to the preparation of therapeutic radiopharmaceuticals. Specifically, the invention relates to the preparation of rhenium therapeutic agents.

BACKGROUND OF THE INVENTION

Therapeutic radiopharmaceuticals generally incorporate a strong beta or alpha emitting radionuclide. Severe chemical damage may be caused by such radionuclides if the radionuclides are not handled properly. Radioactive pharmaceuticals, however, are widely used for diagnosis and treatment of certain illnesses such as cancer and heart disease. For diagnostic purposes, radioactive complexes have been used to provide both negative and positive images of body organs, skeletal images and the like.

For most applications of radiopharmaceuticals, the nonradioactive portion of the complex to be used is prepared and stored until time for administration to the patient, at which time the radioactive portion of the complex is added to form the radiopharmaceutical of interest. Examples of this are disclosed in U.S. Pat. Nos. 3,983,227 (1976) and 4,652,440 (1987). Further, in many situations, the radioactive component of the complex must be generated and/or purified at the time the radiopharmaceutical is prepared for administration to the patient. U.S. Pat. No. 4,778,672, assigned to the University of Cincinnati, (1988) describes, for example, a method for purifying pertechnetate and perrhenate for later use in a radiopharmaceutical. EP 250966, also assigned to the University of California (1988) describes a method for obtaining a sterile, purified complexed radioactive perrhenate from a mixture which includes, in addition to the ligand-complexed radioactive perrhenate, uncomplexed ligand, unligated perrhenate, rhenium dioxide and various other compounds. Specifically, the application teaches a method for purifying a complex of rhenium-186 and 1-hydroxyethylidene diphosphonate (HEDP) from a crude solution. In the process of forming the complex, high quantities of reductant are required for the reduction of perrhenate to achieve chelation. This process results in excess ligand and reductant in the crude solution. Partially because of the necessity of removing excess ligand and reductant to avoid high uptake of the radioactive complexes in soft tissue, further purification of the rhenium complex (the rhenium is in the form of radioactive ligand-complexed perrhenate) by a low pressure or gravity flow chromatographic procedure is required. Another reason for purification by anion exchange chromatography of the crude rhenium solution is to remove the unstable species and obtain the more thermodynamically stable product. This purification involves the aseptic collection of several fractions which elute from the separation medium used in the particular chromatographic procedure, followed by a determination of exactly which fractions to combine. After combining the selected fractions, the fractions are sterile filtered and diluted prior to injection into the patient. The purified rhenium complex must be injected into the patient within one hour of preparation to avoid the possibility of degradation. Thus, a rhenium complex may have to be purified twice before use, causing inconvenience and possible dangers to the user.

There is a need in the art for a method of preparing a stabilized radio-pharmaceutical ready for use in diagnostic or therapeutic applications. Further, there is a need in the art for a method of preparing rhenium therapeutic agents that do not need to undergo a purification step prior to use.

SUMMARY OF THE INVENTION

The present invention is directed to a process for preparing a rhenium therapeutic agent which does not require purification prior to administration to a living being.

The process by which the rhenium therapeutic agents are prepared includes using controlled concentrations of the reactants such that substantially all of the rhenium starting material is reduced and coordinated with a desired ligand. The process of the present invention comprises:

(a) preparing a first aqueous solution of rhenium in the form of radioactive perrhenate, the concentration of rhenium in said solution within the range of about $5.0 \times 10^{-6}$ M to about $2.0 \times 10^{-3}$ M; and (b) reducing and complexing the radioactive perrhenate by mixing with the first solution a second solution or lyophilized solid comprising a ligand which complexes with the radioactive perrhenate and a reductant, wherein the reductant is present in the second solution at a concentration in the range of about 0.005M to about 0.020M and the ligand is present in the second solution at a concentration in the range of about 0.01M to about 0.15M;

wherein the pH of the resultant solution is within the range of about 1.5 to about 5.5.

DETAILED DESCRIPTION OF THE INVENTION

According to the process of this invention, the concentration of the ligand used to form a complex for use as a therapeutic agent is kept between about 0.01M and 0.15M. Since the concentration of ligand is relatively low, the resulting solutions will contain much less excess ligand than in the prior art processes and the concentrations of reductant and rhenium used also can be lower than previously believed possible. The process surprisingly results in substantially complete reduction and coordination of the rhenium.

Previous studies had indicated that high concentrations of reductant were required for the reduction of perrhenate to achieve chelation. In the present process, high concentrations of reductant are not required for substantially complete reduction of the rhenium. Without excess ligand and reductant in the solution, the rhenium complex prepared can be administered directly to a living being without having to undergo a further purification step for the removal of excess ligand and reductant.

Without wanting to be bound by theory, it is believed that the concentrations of the reactants (i.e. perrhenate, reductant and ligand) are important in determining the species of complexes formed. As the reaction conditions are varied, different species of complexes can be formed. Larger forms of the rhenium complexes are believed to be formed at relatively higher concentrations of reactants. These larger molecules decrease the effectiveness of the rhenium complexes by reducing the amount of complex that can reach the appropriate area of the body to be imaged and dosed.

It also is theorized that pH is important to the formation of rhenium complexes. At lower pH, rhenium is more efficiently reduced, affecting the ability of the rhenium to form specific complex structures with the ligand. Also, since rhenium is more efficiently reduced at lower pH's, less reductant may be required. However, the ability of chelation of the ligand to the reduced perrhenate also may be influenced by the solution pH, so a compromise for optimal pH for effective reduction of perrhenate and ligand coordination must be found.

Thus, the process of the present invention by which the rhenium therapeutic agents are prepared includes using controlled concentrations of the reactants such that substantially all of the rhenium starting material is reduced and coordinated with a desired ligand. The process further includes controlling pH for efficient reduction of the rhenium. The process includes preparing a first aqueous solution of rhenium in the form of radioactive perrhenate, wherein the concentration of rhenium in the solution is within the range of about $5 \times 10^{-6}$M to about $2 \times 10^{-3}$M, and then reducing and complexing the radioactive perrhenate by mixing the first solution with a second solution or lyophilized solid of a second solution. The second solution or lyophilized solid comprises a ligand which complexes with the radioactive perrhenate and a reductant wherein the reductant is present in the second solution at a concentration in the range of about 0.005M and about 0.020 M and the ligand is present in the second solution at a concentration in the range of about 0.01M and about 0.15 M. The pH of the resultant solution is within the range of about 1.5 to about 5.5. The lyophilized solid is prepared by first forming a second solution with the concentrations as noted and then lyophilizing to form a solid.

The rhenium for use in the process of this invention is obtained through methods known in the art. Typically, Re-186 is formed by irradiating rhenium (Re-185) with a strong neutron radiation. In general, a radiation having a flux of $10^{14}$ neutrons $cm^{-2}s^{-1}$ will form Re-186. The Re-186 metal can be oxidized by a strong oxidant, such as hydrogen peroxide, nitric acid, and the like. This forms a solution of perrhenate ($ReO_4^-$). This solution then can be neutralized with a strong base, such as ammonia, or a strong acid, such as hydrochloric acid or sulfuric acid, as required. The formed solution includes perrhenate-186 together with the by-products of the oxidation of the rhenium metal along with the salts generated by the neutralization.

An aqueous crude solution of perrhenate-188 can be formed in this same manner with the exception that the rhenium starting material would be Re-187 rather than Re-185. A more preferred method for obtaining Re-188 is by eluting a tungsten-188/Re-188 generator with a saline solution or the like.

The perrhenate generated as described above can be further purified. One method of purification is described in U.S. Pat. No. 4,778,672, incorporated herein in its entirety, which discloses the use of a lipophilic counter cation to separate the perrhenate from an aqueous mixture of crude perrhenate by preferential sorption in a liquid-liquid or liquid-solid separation.

The unpurified or purified perrhenate then can be reduced and complexed with a selected ligand. Specifically, a first aqueous solution of rhenium in the form of radioactive perrhenate is prepared wherein the rhenium preferably is present in a concentration between about $5 \times 10^{-6}$M and $2 \times 10^{-3}$M. The first aqueous solution is at a pH of about 1.0 to about 8.0. This first aqueous solution is combined with a second solution or lyophilized solid of a ligand and a reductant. Optionally, a buffer and/or an antioxidant such as ascorbic acid, gentisic acid or p-aminobenzoic acid is added to the second solution. Suitable reductants include stannous chloride, sodium borohydride, sodium dithionite, tin metal and formamidine sulfinic acid. The preferred reductant for the process of this invention is stannous chloride. The desirable concentration of reductant is between about 0.005M and 0.020 M. The ligand to be used is one which complexes with radioactive perrhenate.

The ligands which may be complexed with the rhenium include phosphonates useful as agents for bone cancer, sulfur colloids useful for radiation synovectomy treatment of arthritic joints and monoclonal antibodies useful for treatment of cancerous tumors. Ligands useful as bone-scanning agents are preferred. A broad range of mono-, di- and polyphosphonic acids and their pharmaceutically acceptable salts are known to concentrate on the skeleton upon injection of solutions thereof into a patient. Also, carboxylates, dicarboxylates and polycarboxylates which are useful as bone-scanning agents may be useful as ligands. Acceptable ligands include polyphosphates, pyrophosphates, phosphonates, diphosphonates, phosphonites and imidophosphonites. Preferred ligands are 1-hydroxyethylidene diphosphonate (HEDP), methylene diphosphonate (MDP), (dimethylamino)methyl diphosphonate (DMAD), (hydroxy)methyldiphosphonate (HMDP), and ethylene diamine tetramethyl phosphonate (EDTMP). In the preferred embodiment, the ligand is present in a concentration of between about 0.01M and 0.15 M. The pH of the second solution or the pre-lyophilized solution is in the range of about 1.5 and 5.5.

The radioactive perrhenate is reduced and complexed by mixing the first solution with the second solution or lyophilized solid. The pH of the resultant solution is within the range of about 1.5 to about 5.5. The pH preferably will be between about 2.0 and 2.5.

The process of the present invention is particularly suitable for use in the preparation of a kit for use by radiopharmaceutical laboratories. The kit can preferably include about 2 to 20 mg of ligand and about 2.0 to 5.0 mg of a reductant in an aqueous solution wherein the ligand is present in a concentration between about 0.01M and 0.15M, and the reductant is present in a concentration between about 0.005M to 0.020M. Optionally, about 0.5 to 5 mg anti-oxidant in a concentration of between about $3 \times 10^{-3}$M and $3.5 \times 10^{-2}$ M can be provided in the aqueous solution. The anti-oxidant preferably is present at a concentration of about 0.020M. At the laboratory, a solution of perrhenate is obtained and added to the other kit components. The rhenium concentration of the perrhenate should be between about $5 \times 10^{-6}$M and $2 \times 10^{-3}$M. The mixture then is heated to between about 80° C. and 100° C. for about 10 to 30 minutes to achieve complete reduction and chelation. The optimal temperature and heating time for a particular ligand within these guidelines can be easily determined by persons with ordinary skill in the art. The pH of the resulting solution will be about 1.5 to 5.5. Thus, addition of a buffer solution to adjust the pH of the resultant rhenium solution to between about 4.0 to 8.0 may be needed before injection. The final pH preferably will be between 5.0 and 6.0.

The following example further illustrates the process of this invention, but is not meant to limit the scope of the invention in any way.

EXAMPLE

The following procedure and quantities of ligand, tin and anti-oxidant were used to prepare a $^{186}$Re-HEDP agent with less than 1% $ReO_4^-$. Ten milligrams of $Na_2H_2HEDP$, 3.5 mg $SnCl_2\cdot 2H_2O$ and 3 mg gentisic acid were mixed together. Then, 0.9 ml of degassed saline was added and the solution was sonicated for about 1 minute. A solution of 0.2 ml $ReO_4^-$ in ethanol was added. The solution contained about 0.11 mg total rhenium (185, 186, 187), ($6\times 10^{-4}$M) and about 2mCi of Re-186. The pH of the solution was 2.65. The solution was heated for 20 minutes at 100° C. in an oil bath. The solution then was removed and cooled to room temperature and the pH adjusted to about 5.5 with 1M NaOH solution.

Analysis by HPLC and paper chromatography indicated a pure product with <1% perrhenate and <0.5% rhenium dioxide. These results are nearly identical to those obtained for $^{186}$Re-HEDP prepared by the methods discussed above in U.S. Pat. No. 4,778,672 and disclosed in EP 250966, which include the purification of the crude material by anion exchange chromatography.

I claim:

1. A process for preparing a rhenium therapeutic agent which does not require purification prior to administration comprising:
   (a) preparing a first aqueous solution of rhenium in the form of radioactive perrhenate, the concentration of rhenium in said solution within the range of about $5\times 10^{31\ 6}$M to about $2\times 10^{-3}$M; and
   (b) reducing and complexing the radioactive perrhenate by mixing the first solution with either a second solution or a lyophilized solid form thereof, said second solution or said solid comprising a ligand which complexes with the radioactive perrhenate and a reductant wherein the reductant is present at a concentration in the range of about 0.005M to about 0.020M and the ligand is present at a concentration in the range of about 0.01M to about 0.15M;

wherein the pH of the resultant solution is within the range of about 1.5 to about 5.5.

2. The method of claim 1 wherein the radioactive perrhenate contains either $Re^{186}$ or $Re^{188}$.

3. The method of claim 1 wherein the pH is between 2.0 and 2.5.

4. A process according to claim 1 wherein said second solution of lyophilized solid further comprises an antioxidant.

5. A process according to claim 1 wherein the reductant is stannous chloride.

6. The method of claim 1 wherein the ligand is a bone seeking ligand.

7. The method of claim 6 wherein the ligand is a polyphosphate, pryophosphate, phosphonate, diphosphonate, phosphonite or imidodiphosphate.

8. The method of claim 7 wherein the ligand is a diphosphonate.

9. The method of claim 8 wherein the ligand is 1-hydroxyethylidene diphosphonate.

* * * * *